United States Patent [19]

Smith

[11] 4,136,099

[45] Jan. 23, 1979

[54] PRODUCTION OF TETRAHYDROFURAN FROM 1,4-BUTANEDIOL USING TUNGSTEN ON ALUMINA CATALYSTS

[75] Inventor: William E. Smith, Schenectady, N.Y.

[73] Assignee: General Electric Company, Pittsfield, Mass.

[21] Appl. No.: 862,584

[22] Filed: Dec. 20, 1977

Related U.S. Application Data

[63] Continuation of Ser. No. 635,730, Nov. 26, 1975, abandoned.

[51] Int. Cl.$^2$ ............................................. C07D 307/08
[52] U.S. Cl. .................................................. 260/346.11
[58] Field of Search .................................... 260/346.11

[56] References Cited

U.S. PATENT DOCUMENTS

| 2,251,835 | 8/1941 | Reppe et al. ................... 260/346.11 |
| 2,251,895 | 9/1941 | Reppe et al. ................... 260/346.11 |

OTHER PUBLICATIONS

Murata et al., Chem. Abstracts, vol. 78, (1973), 147773.

*Primary Examiner*—Henry R. Jiles
*Assistant Examiner*—Bernard Dentz
*Attorney, Agent, or Firm*—Morgan, Finnegan, Pine, Foley & Lee

[57] ABSTRACT

An improved process for producing tetrahydrofuran from 1,4-butanediol, the improvement comprising carrying out the dehydration in the presence of a tungsten oxide catalyst.

2 Claims, No Drawings

PRODUCTION OF TETRAHYDROFURAN FROM 1,4-BUTANEDIOL USING TUNGSTEN ON ALUMINA CATALYSTS

This is a continuation, of application Ser. No. 635,730 filed Nov. 26, 1975 now abandoned.

This invention relates to an improved process for producing tetrahydrofuran from 1,4-butanediol, the improvement comprising carrying out the dehydration in the presence of a tungsten oxide catalyst.

BACKGROUND OF THE INVENTION

It is known in the art that tetrahydrofuran can be produced by a number of different methods, the more prominent among them the dehydration of 1,4-butanediol and the catalytic hydrogenation of furan. Most tetrahydrofuran is, in fact, manufactured in a multi-step sequence starting with the reaction of acetylene and formaldehyde in the presence of a cuprous acetylide complex to form butynediol. The butynediol is hydrogenated to butanediol, which is dehydrated to tetrahydrofuran as indicated above. As disclosed in copending applications of William E. Smith Ser. Nos. 623,904 and 623,905, filed on Oct. 20, 1975, both titled A Process for Preparing Tetrahydrofuran and assigned to the same assignee as the present invention and now U.S. Pat. Nos. 4,011,244 and 4,010,171 respectively, tetrahydrofuran can also be produced by dehydroacyloxylation of carboxylate esters of 1,4-butanediol.

In addition, tetrahydrofuran can be prepared by catalytic hydrogenation of maleic, fumaric and succinic acids, their respective anhydrides and ester derivatives, and butyrolactone.

Methods for effecting the dehydration of 1,4-butanediol to tetrahydrofuran previously disclosed include the use of alumina and phosphoric acid catalysts (U.S. Pat. No. 2,251,835), and silica-alumina catalysts (Japanese Patent 73 01 075).

Tetrahydrofuran is a useful solvent for natural and synthetic resins and is a valuable intermediate in manufacture of a number of chemicals and plastics.

DESCRIPTION OF THE INVENTION

It has been discovered that tetrahydrofuran can be produced from 1,4-butanediol in an improved process which employs a class of heterogeneous catalysts based on the partly reduced oxide or oxides of tungsten. The method is characterized by high reaction efficiency; the catalysts are extremely active, selective and long-lived. Yields of tetrahydrofuran are essentially quantitative in both liquid phase and vapor phase modifications.

The catalysts that may be within the scope of the instant invention include all tungsten oxide compounds, including tungstic oxide, tungstic acid, partly reduced tungsten oxide and tungstic acid derivatives, and mixtures thereof. The scope of the instant invention also includes the use of active support materials, such as alumina, silica, silica-alumina and the like in combination with the tungsten oxide compounds, as well as inert support materials.

The partly reduced "blue oxide" of tungsten has been recognized for many years as a powerful agent for dehydrating alcohols to olefins. This substance was until more recent years formulated as $W_2O_5$; it is now commonly accepted as having the composition $W_{20}O_{58}$.

In the vapor phase modification, the active catalyst may be prepeared in place by reducing a bed of supported or unsupported tungstic oxide ($WO_3$) in a stream of hydrogen or vapor of 1,4-butanediol or other alcohol. In the liquid phase modification, the catalyst may be prepared in situ by heating tungstic oxide, tungstic acid ($H_2WO_4$), or either of these substances compounded with a support such as alumina, silica, or the like in the presence of the 1,4-butanediol, optionally in a hydrogen atmosphere. In both the vapor phase and liquid phase methods, the active catalyst is a partly reduced tungsten oxide.

When the tungsten oxide catalyst is supported on alumina or silica or the like, a synergistic activating effect may be achieved. Thus a catalyst prepared from a composition of 10% tungstic oxide and 90% aluminum oxide is substantially more active than one derived from tungstic oxide itself. Alumina, silica, silica-alumina and other such oxide supports are themselves catalysts for the dehydration of 1,4-butanediol, but are substantially less active than the partly reduced tungsten oxide, supported or unsupported.

The temperature at which the disclosed process may be carried out varies from about 150° C. to about 350° C. Preferably, the dehydration is effected in the temperature range of 175° C. to 275° C. The maximum temperature depends upon destruction of the product, olefin formation occurring under too rigorous conditions.

In a preferred embodiment, a bed of a tungstic oxide catalyst is reduced in place by heating under a hydrogen stream, and 1,4-butanediol is passed through with a hydrogen or hydrogen-containing carrier gas at about 220° C. The converison to tetrahydrofuran and water is complete in a single pass at a liquid hourly space velocity (LHSV) as high as 5.0.

In another preferred embodiment, a mixture of 1,4-butanediol and about 10% by weight of tungstic acid is heated at about 200° C. under 1000 psi of hydrogen pressure for about two hours. A high degree of conversion to tetrahydrofuran free of by-products is achieved.

Well known techniques may be employed to obtain the tetrahydrofuran in anhydrous form.

DESCRIPTION OF THE PREFERRED EMBODIMENT

The following examples are set forth to illustrate more clearly the principle and practice of this invention to those skilled in the art. Unless otherwise specified, where parts or percents are mentioned, they are parts or percents by weight.

The vapor phase processes to be described were carried out using a 20 mm ID × 30 cm effective length vertical hot tube reactor (70 cc effective volume), constructed from heavy wall glass, with 24/40 male and female joints. Vigreaux points were indented just about the male joint to support catalyst pellets. Thermocouple leads were fastened into three other Vigreaux indentations at points along the length. Briskheat glass insulated heating tapes were wound onto the tube, covered with glass wool and glass tape, and connected to separate variable transformers. The tube exit was connect by a gooseneck (also heated) to an efficient condenser and collection vessel. An electrically heated three-necked flask served as the evaporator, with the reactants added through a side neck by a syringe pump. A hydrogen stream (one bed volume per minute) served as the carrier gas.

The liquid phase processes to be described were carried out using an Autoclave Engineers 300 cc Magnedrive autoclave.

EXAMPLE 1

The tube reactor was charged with 162 grams (70 ml) of Harshaw tungsten catalyst WO602, ⅛ inch pellets containing 95% $WO_3$. The bed was heated to 250° C. under a hydrogen stream of 70 ml per minute. Then 1,4-butanediol was passed into the boiler at 36 ml per hour. When a steady state was reached, the condensed effluent contained only tetrahydrofuran and water in 1:1 ratio as determined by glpc and nmr analysis. Operation at 220° C. afforeded the same results. The catalyst showed no sign of deactivation even after intermittent and prolonged use at various temperatures.

The used catalyst was intensely blue, characteristic of the $W_{20}O_{58}$ commposition.

EXAMPLE 2

The process was carried out as in Example 1 using a bed of Harshaw 0801 tungsten catalyst, ⅛ inch pellets composed of 10% $WO_3$ and 90% $Al_2O_3$. This catalyst was extremely active in promoting the dehydration; operation at 250° C. and a LHSV as high as 5 afforded the 1:1 tetrahydrofuran-water mixture completely free of unconverted butanediol.

EXAMPLE 3

The autoclave was charged with 150 grams of 1,4-butanediol and 15.0 grams of tungstic acid ($H_2WO_4$), then heated at 200° C. under 1000 psi of hydrogen with 1000 rpm stirring for two hours. Quantitative glpc analysis of the liquid phase showed the presence of 10.4 grams of butanediol (6.9% unconverted) and 112 grams of tetrahydrofuran (100% yield based on 93% conversion).

The catalyst, isolated as an intensely blue, insoluble material, retained its activity on repeated use.

EXAMPLE 4

This example is intended to demonstrate the superior activity of the tungsten oxide catalysts in tetrahydrofuran formation from 1,4-butanediol in comparison to silica-alumina, a widely employed dehydration catalyst.

The autoclave was charged with 150 grams of 1,4-butanediol and 15.0 grams of Davison Grade 970 silica-alumina powder (83% $SiO_2$, 17% $Al_2O_3$), then heated at 200° C. under autogenous pressure for two hours. Quantitative glpc analysis of the liquid phase showed the presence of 91.4 grams of unreacted butanediol (60% unconverted) and 46.1 grams of tetrahydrofuran (98.3% yield based on 39.1% conversion).

It will thus be seen that the objects set forth above among those made apparent from the preceding description are efficiently attained and since certain changes may be made in carrying out the above process and in the composition set forth without departing from the scope of this invention, it is intended that all matters contained in the above description shall be interpreted as illustrative and not in a limiting sense.

What is claimed is:

1. An improved process for producing tetrahydrofuran by heating 1,4-butanediol at a temperature of from about 150° C. to about 350° C. in the presence of a catalyst, the improvement comprising using a heterogeneous tungsten oxide catalyst on an active support which is alumina and conducting the dehydration under pressure in the presence of hydrogen.

2. A process as defined in claim 1 wherein the temperature is in the range of 175° to 275° C.

UNITED STATES PATENT AND TRADEMARK OFFICE
CERTIFICATE OF CORRECTION

PATENT NO. : 4,136,099
DATED : Jan. 23, 1979
INVENTOR(S) : William E. Smith

It is certified that error appears in the above-identified patent and that said Letters Patent are hereby corrected as shown below:

Col. 2, line 59, "connect" should read
-- connected --

Col. 4, line 14, "60%" should read
-- 60.9% --

Signed and Sealed this

Tenth Day of July 1979

[SEAL]

Attest:

LUTRELLE F. PARKER
Attesting Officer     Acting Commissioner of Patents and Trademarks